United States Patent
Coggan et al.

(10) Patent No.: US 7,438,981 B2
(45) Date of Patent: Oct. 21, 2008

(54) INDENOFLUORENE COMPOUNDS AND ORGANIC ELECTROLUMINESCENT DEVICES USING THE SAME

(75) Inventors: Jennifer A. Coggan, Cambridge (CA); Nan-Xing Hu, Oakville (CA); Hany Aziz, Oakville (CA)

(73) Assignee: LG. Philips LCD Co., Ltd., Seoul (KR)

( * ) Notice: Subject to any disclaimer, the term of this patent is extended or adjusted under 35 U.S.C. 154(b) by 393 days.

(21) Appl. No.: 11/312,446

(22) Filed: Dec. 21, 2005

(65) Prior Publication Data

US 2007/0141389 A1 Jun. 21, 2007

(51) Int. Cl.
- *H01L 51/54* (2006.01)
- *C09K 11/06* (2006.01)
- *C07F 7/08* (2006.01)
- *C07F 5/02* (2006.01)

(52) U.S. Cl. .............. 428/690; 428/917; 313/504; 313/506; 257/40; 556/406; 556/431; 556/432; 568/3

(58) Field of Classification Search .......... 313/504, 313/506; 556/406, 431, 432; 568/3
See application file for complete search history.

(56) References Cited

U.S. PATENT DOCUMENTS

| | | |
|---|---|---|
| 3,172,862 A | 3/1965 | Gurnee et al. |
| 4,356,429 A | 10/1982 | Tang |
| 4,539,507 A | 9/1985 | VanSlyke et al. |

(Continued)

OTHER PUBLICATIONS

Tang et al. "Electroluminescence of doped organic thin films", J. Appl. Phys. 85 (9), vol. pp. 3610 to 3616 (May 1, 1989).

(Continued)

*Primary Examiner*—Dawn Garrett
(74) *Attorney, Agent, or Firm*—McKenna Long & Aldridge LLP

(57) ABSTRACT

An organic electroluminescent material and a device using the same wherein the electroluminescent material is a charge transport indenofluorene selected from one of Formula (I) and Formula (II)

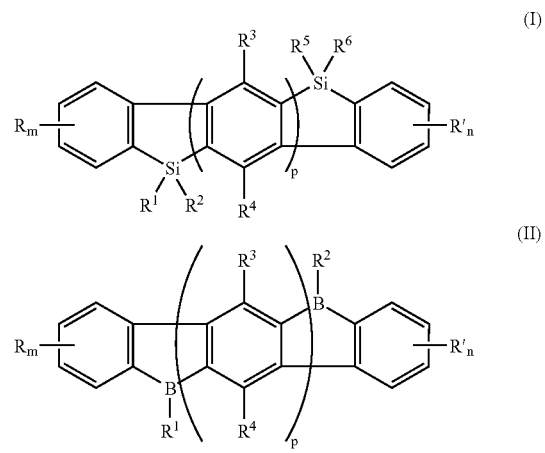

wherein R and R' are independently selected from the group consisting of a hydrogen atom, halogen atom, cyano, alky, alkoxyl, alicyclic alkyl, substituted or unsubstituted aryl or heteroaryl, and dialkylamino; m and n are numbers of 0 to 4; $R^1$, $R^2$, $R^5$, and $R^6$ are independently selected from the group consisting of hydrogen, an alkyl, a substituted or unsubstituted aryl, or an heteroaryl, an alkoxy, and vinyl; $R^3$ and $R^4$ are independently selected from the group consisting of a hydrogen atom, halogen atom, alkyl, alkoxy, and substituted or unsubstituted aryl or heteroaryl; and p is 1 or greater.

43 Claims, 1 Drawing Sheet

U.S. PATENT DOCUMENTS

| | | |
|---|---|---|
| 4,720,432 A | 1/1988 | VanSlyke et al. |
| 4,885,211 A | 12/1989 | Tang et al. |
| 5,150,006 A | 9/1992 | VanSlyke et al. |
| 5,151,629 A | 9/1992 | VanSlyke |
| 5,409,783 A | 4/1995 | Tang et al. |
| 5,429,884 A | 7/1995 | Namiki et al. |
| 5,487,953 A | 1/1996 | Shirota et al. |
| 5,516,577 A | 5/1996 | Matsuura et al. |
| 5,554,450 A | 9/1996 | Shi et al. |
| 5,942,340 A | 8/1999 | Hu et al. |
| 6,479,172 B2 | 11/2002 | Hu et al. |
| 2004/0109955 A1* | 6/2004 | Kitano et al. ............... 428/1.1 |
| 2005/0170202 A1* | 8/2005 | Tamao et al. ............... 428/690 |

OTHER PUBLICATIONS

Saito et al. "Design of Organic Electroluminescent Materials and Devices" Molecular Crystals and Liquid Crystals, Mol. Cryst. Liq. Cryst., vol. 253, pp. 125 to 132 (1994).

Brassard and L'Ecuyer, "L'Arylation Des Quinones Par Les Sels De Diazonium", Can. J. Chem., vol. 36, pp. 709-711 (1958).

* cited by examiner

INDENOFLUORENE COMPOUNDS AND ORGANIC ELECTROLUMINESCENT DEVICES USING THE SAME

BACKGROUND OF THE INVENTION

1. Field of the Invention

The present invention is generally directed to electroluminescent (EL) devices, or members, and more specifically, to compounds and organic EL devices using the same, wherein the devices have enhanced thermal and operational stability, and improved durability. The devices of the present invention contain charge, either hole or electron, transport components or compounds comprised of indenofluorene compounds, such as those of the formulas illustrated herein.

2. Discussion of the Related Art

Typical art organic EL devices contain a laminate comprised of an organic luminescent material and electrodes of opposite polarity. As exemplified by U.S. Pat. No. 3,530,325, these devices include a single crystal material, such as single crystal anthracene, as the luminescent substance reference. However, these devices require excitation voltages on the order of about 100 volts or greater. One way to improve device performance has been to incorporate additional layers such as charge injecting and charge transport layers.

Illustrative examples of EL devices are disclosed in publications by Tang et al. in J. Appl. Phys., vol. 65, pp. 3610 to 3616 (1989) and Saito et al. in Mol. Cryst. Liq. Cryst., vol. 253, pp. 125 to 132 (1994), the disclosures of which are fully incorporated herein by reference.

A dual layer organic EL device is typically comprised of one hole transport layer adjacent to the anode supporting hole injection and transport, and an electron transport layer adjacent to the cathode supporting electron injection and transport. In this type of structure, the recombination of charge carriers and subsequent emission of light occurs in one of these layers near their interface. Optionally, a fluorescent material which is capable of emitting light in response to electron-hole recombination can be added to one of said layers.

In another typical configuration, an EL device can be comprised of three separate layers, a hole transport layer, an emission layer, and an electron transport layer, which are laminated in sequence, and are sandwiched as a whole between an anode and a cathode.

Specifically, U.S. Pat. No. 4,356,429 discloses an EL device formed of an organic luminescent medium consisting of a hole transporting layer and an electron transporting layer, wherein the hole transporting layer is comprised of a porphyrinic compound. Further, U.S. Pat. No. 4,539,507 discloses using a substituted aromatic tertiary amine layer for the hole transporting porphorinic layer. Illustrative examples of the aromatic tertiary amine compounds disclosed in the '507 patent are triphenylamines, such as N,N,N-triphenylamine and N,N,N-tri-p-tolylamine, those containing at least two aromatic tertiary amine moieties such as 1,1-bis(4-di-tolylaminophenyl)cyclohexane, and tetraaryidiamines such as N,N'-bis(3-methylphenyl)-N,N'-diphenyl-4,4'-diaminobiphenyl, N,N,N'N'-tetra-p-tolyl-4,4'-diaminobiphenyl. Also, of interest with respect to EL devices are U.S. Pat. Nos. 5,487,953 and 5,554,450.

While hole transport materials comprised of the above-mentioned aromatic tertiary amines are generally known to facilitate hole injection and hole transport processes, the thermal and morphological instabilities of these materials as the hole transport layers have led to relatively poor EL performance and short operational life. There is also a need to develop hole transport materials which are readily accessible synthetically, and which can be prepared in high yields and with excellent electronic purity. Another need resides in the provision of new hole transport materials which are capable of forming thermally and morphologically stable thin films by for example, vacuum deposition techniques. A still further need is the preparation of new hole transport materials suitable for organic EL device applications, and which materials possess excellent hole transport characteristics, enabling the EL devices to operate at low voltages of, for example, below 20 volts. These and other needs can be achievable with the EL devices of the present invention in embodiments thereof.

In U.S. Pat. No. 4,539,507 there is disclosed an EL device formed of a conductive glass transparent anode, a hole transporting layer of 1,1-bis(4-p-tolylaminophenyl)cyclohexane, an electron transporting layer of 4,4'-bis(5,7-di-tert-pentyl-2-benzoxzolyl)stilben, and an indium cathode.

There has been an increased interest in developing energy-efficient flat-panel displays based on organic EL devices primarily because of their potential as an emissive display technology which offers unrestricted viewing angles and high luminescence output at low operating voltages. However, while recent progress in organic EL research has elevated the potential of organic EL devices for widespread applications, the performance levels of a number of current available devices, especially with respect to blue emission, may still be below expectations.

Further, for visual display applications, organic luminescent materials should provide a satisfactory color in the visible spectrum, normally with emission maxima at about 460, 550 and 630 nanometers for blue, green and red. These organic EL devices may comprise a light-emitting layer which is comprised of a host material doped with a guest fluorescent material that is responsible for color emission. For efficient down-shifting of EL emission wavelength in the host-guest emitting layer, it may be desirable that the host material should fluorescence in the blue or shorter wavelength region.

In many conventional organic EL devices, the luminescent zone or layer is formed of a green-emitting luminophor of tris(8-hydroxyquinolinate)aluminum with certain fluorescent materials. U.S. Pat. No. 5,409,783 discloses a red-emitting organic EL device by doping the tris(8-hydroxyquinolinate) aluminum layer with a red fluorescent dye. However, up-shifting of the tris(8-hydroxyquinolinate)aluminum emission to blue region is believed to be highly inefficient.

Although there have been several disclosures describing blue-emitting organic EL devices, for example in U.S. Pat. Nos. 5,151,629 and 5,516,577, the disclosures of which are fully incorporated herein by reference, their performance characteristics still possess many disadvantages such as poor emission hue, high operation voltages, low luminance, and poor operation stability.

Thus, there continues to be a need for improved luminescent compositions for organic EL devices, which may be vacuum evaporable and form thin films with excellent thermal stability. There is also a need for luminescent compositions which are capable of providing uniform and satisfactory emission in the blue region of the light spectrum. In particular, there is a need for efficient blue luminescent materials for organic EL devices, which may optionally be doped with a fluorescent dye. Further, there is also a need for luminescent compositions which can enhance charge transporting characteristics, thus lowering device driving voltages.

The rectification of all these performance deficiencies represents one formidable challenge in EL device research and development. Accordingly, one of the features of the present invention in embodiments thereof is to provide an organic compound, and EL devices using such compound, which provide extended device life span and excellent EL efficiency.

SUMMARY OF THE INVENTION

Accordingly, the present invention is directed to new indenofluorene compounds and organic EL devices using the same that substantially obviates one or more of the problems due to limitations and disadvantages of the related art.

One advantage of the present invention is that it can provide organic EL devices with enhanced thermal stability and operational stability.

Another advantage of the present invention is that it can provide novel performance enabling charge transport materials for organic EL devices.

Another advantage of the present invention is that it can provide improved EL devices which exhibit high electroluminescence efficiency at relatively low operating voltages.

Another advantage of the present invention is that it can provide improved EL devices comprised of an anode, a cathode, and an organic electroluminescent element sandwiched in between the anode and the cathode, and wherein the organic electroluminescent element is comprised of at least one layer containing a silicon bridged indenofluorene hole transport component.

Another advantage of the present invention is that it can provide improved EL devices comprised of an anode, a cathode, and an organic electroluminescent element sandwiched in between the anode and the cathode, and wherein the organic electroluminescent element is comprised of at least one layer containing a boron bridged indenofluorene electron transport component.

Another advantage of the present invention is that it can provide EL devices with indenofluorene derivative compounds which possess excellent charge transporting capabilities, superior thermal stability, and can be vacuum deposited as thin film EL hole transport components.

To achieve these and other advantages and in accordance with exemplary embodiments of the present invention, as embodied and broadly described, an organic electroluminescent device comprising an anode, a cathode, and a charge transfer component selected from one of Formula I or Formula II:

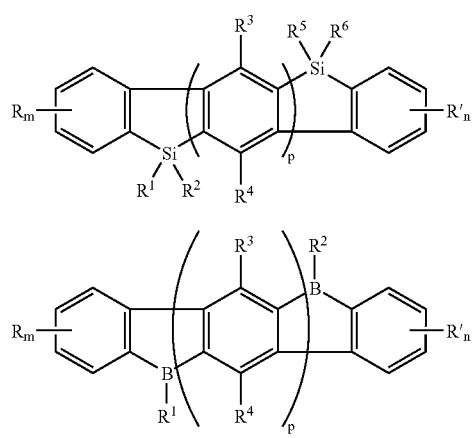

wherein R and R' are independently selected from the group consisting of a hydrogen atom, halogen atom, cyano, alkyl, alkoxyl, alicyclic alkyl, substituted or unsubstituted aryl or heteroaryl, and dialkylamino; m and n are numbers of 0 to 4; $R^1$, $R^2$, $R^5$, and $R^6$ are independently selected from the group consisting of hydrogen, an alkyl, a substituted or unsubstituted aryl, or an heteroaryl, an alkoxy, and vinyl; $R^3$ and $R^4$ are independently selected from the group consisting of a hydrogen atom, halogen atom, alkyl, alkoxy, and substituted or unsubstituted aryl or heteroaryl; and p is 1 or greater.

In another aspect of the present invention, an organic electroluminescent compound comprising Formula I:

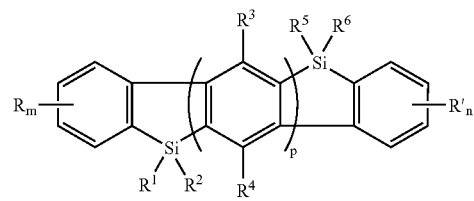

wherein R and R' are independently selected from the group consisting of a hydrogen atom, halogen atom, cyano, alkyl, alkoxyl, alicyclic alkyl, substituted or unsubstituted aryl or heteroaryl, and dialkylamino; m and n are numbers of 0 to 4; $R^1$, $R^2$, $R^5$, and $R^6$ are independently selected from the group consisting of hydrogen, an alkyl, a substituted or unsubsituted aryl, or an heteroaryl, an alkoxy, and vinyl; $R^3$ and $R^4$ are independently selected from the group consisting of a hydrogen atom, halogen atom, alkyl, alkoxy, and substituted or unsubstituted aryl or heteroaryl; and p is 1 or greater.

In another aspect of the present invention, an organic electroluminescent compound comprising Formula II:

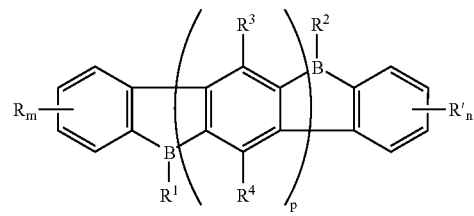

wherein R and R' are independently selected from the group consisting of a hydrogen atom, halogen atom, cyano, alkyl, alkoxyl, alicyclic alkyl, substituted or unsubstituted aryl or heteroaryl, and dialkylamino; m and n are numbers of 0 to 4; $R^1$ and $R^2$ are independently selected from the group consisting of hydrogen, an alkyl, a substituted or unsubstituted aryl, or an heteroaryl, an alkoxy, and vinyl; $R^3$ and $R^4$ are independently selected from the group consisting of a hydrogen atom, halogen atom, alkyl, alkoxy, and substituted or unsubstituted aryl or heteroaryl; and p is 1 or greater.

It is to be understood that both the foregoing general description and the following detailed description are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention.

In the drawings.

DETAILED DESCRIPTION OF THE PREFERRED EMBODIMENTS

Figure 1:
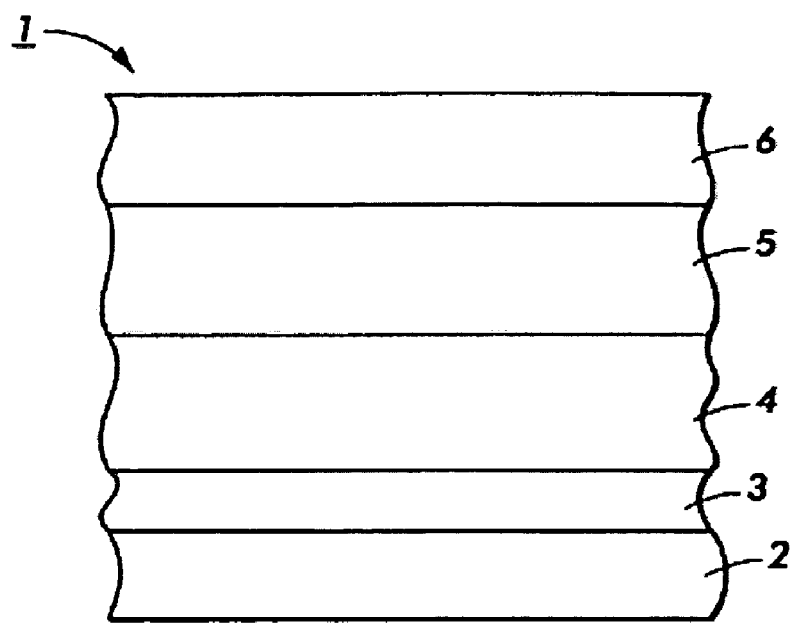
FIG. 1 is an exemplary embodiment of an EL device according to the present invention.

Reference will now be made in detail to exemplary embodiments of the present invention, examples of which are illustrated in the accompanying drawings.

An exemplary embodiment of the novel organic electroluminescent compound of the present invention comprises an indenofluorene of the general Formula I:

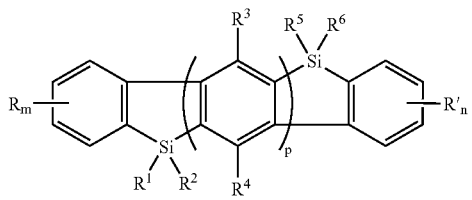

Formula I wherein R and R' are independently selected from the group consisting of a hydrogen atom, halogen atom, cyano, alkyl, alkoxyl, alicyclic alkyl, substituted or unsubstituted aryl or heteroaryl, and dialkylamino; m and n are numbers of 0 to 4; $R^1$, $R^2$, $R^5$, and $R^6$ are independently selected from the group consisting of hydrogen, an alkyl, a substituted or unsubsituted aryl, or an heteroaryl, an alkoxy, and vinyl; $R^3$ and $R^4$ are independently selected from the group consisting of a hydrogen atom, halogen atom, alkyl, alkoxy, and substituted or unsubstituted aryl or heteroaryl; and p is 1 or greater.

Another exemplary embodiment of the novel organic electroluminescent compound of the present invention comprises an indenofluorene of the general Formula II:

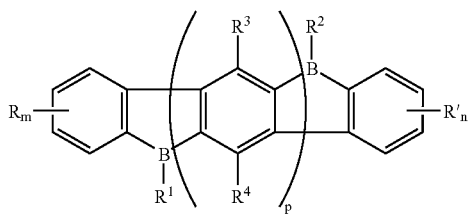

Formula II wherein R and R' are independently selected from the group consisting of a hydrogen atom, halogen atom, cyano, alkyl, alkoxyl, alicyclic alkyl, substituted or unsubstituted aryl or heteroaryl, and dialkylamino; m and n are numbers of 0 to 4; $R^1$ and $R^2$ are independently selected from the group consisting of hydrogen, an alkyl, a substituted or unsubsituted aryl, or an heteroaryl, an alkoxy, and vinyl; $R^3$ and $R^4$ are independently selected from the group consisting of a hydrogen atom, halogen atom, alkyl, alkoxy, and substituted or unsubstituted aryl or heteroaryl; and p is 1 or greater.

As indicated, the indenofluorene compound of the present invention may be bridged with either silicon or boron depending on its application. When bridged with silicon, the compound may be used as a hole transporting material. On the other hand, when bridged with boron, the compound of the present invention may be used as an electron transporting material.

It is within the scope of the present invention to combine various substituent groups with the indenofluorene compound of general Formula (I) and general Formula (II). For example, the aryl groups may contain from 2 to about 30 carbon atoms and may be fused or non-fused aromatic rings such as a benzo, phenyl, naphthyl, thienyl or biphenyl. Additionally, the alkyl groups may contain from 1 to about 25 carbon atoms. Some exemplary alkyl groups include methyl, ethyl, propyl, butyl, pentyl, heptyl, and hexyl. Furthermore, the alkoxy groups may contain from 1 to about 25 carbon atoms. Some exemplary alkoxy groups include methoxy, ethoxy, propoxy, butoxy, pentoxy, and heptoxy. The halogen substituent may be any suitable halogen such as chlorine, bromine, fluorine, or iodine.

In one exemplary embodiment, the indenofluorene compound of the present invention contains one or more alkyl substituent groups having 1 to about 10 carbon atoms, one or more alkoxy substituent groups with 2 to about 12 carbon atoms, and one or more aryl substituent groups with 6 to about 18 carbon atoms.

In yet another exemplary embodiment of the present invention, the indenofluorene compound of general Formula (I) or general Formula (II) may contain one or more alkyl substituents with 1 to about 6 carbon atoms, and one or more alkoxy substituents with 1 to about 6 carbon atoms.

In another exemplary embodiment of the present invention, the indenofluorene compound of general Formula (I) may have R and R' as hydrogen, or alkyl, and $R^1$, $R^2$, $R^5$, and $R^6$ as aryl. Alternatively, R and R' may be hydrogen, or alkyl, and $R^3$ and $R^4$ may be hydrogen atoms. Additionally, $R^1$, $R^2$, $R^5$, and $R^6$ may also be independently selected from the group consisting of phenyl, naphthyl, thienyl and biphenyl.

In another exemplary embodiment of the present invention, the indenofluorene compound of general Formula (II) may have R and R' as hydrogen, or alkyl, and $R^1$ and $R^2$ as aryl. Alternatively, R and R' may be hydrogen, or alkyl, and $R^3$ and $R^4$ may be hydrogen atoms. Additionally, $R^1$ and $R^2$ may also be independently selected from the group consisting of phenyl, naphthyl, thienyl and biphenyl.

In a further exemplary embodiment of the present invention, the indenofluorene compound of Formula (I) may contain an aryl group with 6 to about 30 carbons, wherein $R^1$, $R^2$, $R^5$, and $R^6$ may be aryl groups, R and R' may be hydrogen atoms or methyl groups, and $R^3$ and $R^4$ may be hydrogen atoms.

In a further exemplary embodiment of the present invention, the indenofluorene compound of Formula (II) may contain an aryl group with 6 to about 30 carbons, wherein $R^1$ and $R^2$ may be aryl groups, R and R' may be hydrogen atoms or methyl groups, and $R^3$ and $R^4$ may be hydrogen atoms.

As stated above, the indenofluorene of the general Formula (I) may be used as a hole transporting material, and the indenofluorene of the general Formula (II) may be used as an electron transporting material. Accordingly, various organic EL devices may be constructed using the indenofluorene compounds of general Formula (I) and general Formula (II) of the present invention.

FIG. 1 illustrates an exemplary EL device or organic light emitting diode 1, having a supporting substrate 2 of, for example, glass, an anode 3, a hole transporting layer 4, an electron transporting layer 5, and in contact therewith a cathode 6, such as a low work function metal.

The hole transporting layer 4 and electron transporting layer 5 may be organic materials and either or both may contain the indenofluorene derivative of the present invention. Specifically, the hole transporting layer 4 may contain the silicon bridged indenofluorene compound while the electron transporting layer 5 may contain the boron bridged indenofluorene compound.

In this EL device, a junction is formed between the hole transporting layer, or zone, and the electron transporting layer, or zone. In operation, when the anode is electrically biased with a positive potential with respect to the cathode, holes are injected into the organic hole transporting zone and transported across this zone to the junction. Concurrently, electrons are injected from the cathode into the electron transporting zone and are transported toward the same junction. Recombination of holes and electron occurs near the junction, results in light emission.

Figure 2:
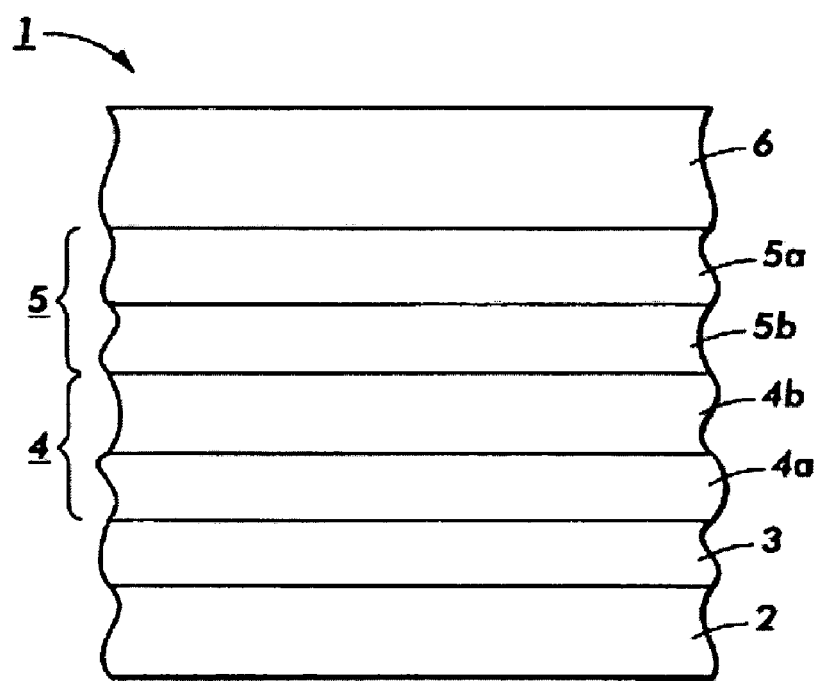
FIG. 2 is another exemplary embodiment of an EL device according to the present invention.

In another embodiment as illustrated in FIG. 2, the light emitting diode 1 is comprised of a supporting substrate 2 of, for example, glass, an anode 3, organic hole transporting zone 4, an organic electron transporting zone 5, and in contact therewith a cathode 6. In this device structure, the transporting zone is comprised of one or more transport layers as opposed to the single layer transporting zone of the device structure of FIG. 1. Specifically, the hole transporting zone 4 of FIG. 2 is comprised of a layer 4a which facilitates hole injection, and a silicon bridged indenofluorene layer 4b which transports hole carriers. The electron transporting zone 5 is comprised of a layer 5a which facilitates electron injection, and a boron bridged indenofluorene layer 5b which transports electrons.

Illustrative examples of the supporting substrate include polymeric components, glass and the like, and polyesters like MYLAR™, polycarbonates, polyacrylates, polymethacrylates, polysulfones, quartz, and the like. Other substrates can also be selected provided, for example, that the material selected can effectively support the other layers, and does not interfere with the device functional performance. The thickness of the substrate can be, for example, from about 25 to about 1,000 microns or more and, for example, from about 50 to about 500 depending, for example, on the structural demands of the device.

Examples of the anode contiguous to the substrate include positive charge injecting electrodes such as indium tin oxide, tin oxide, gold, platinum, or other materials, such as electrically conductive carbon, conjugated polymers such as polyaniline, polypyrrole, and the like, with, for example, a work function equal to, or greater than about 4 electron volts, and more specifically, from about 4 to about 6 electron volts. The thickness of the anode can range from about 10 to about 5,000 Angstroms with the preferred range being dictated by the optical constants of the anode material. One preferred range of thickness is from about 20 to about 1,000 Angstroms.

The hole transporting layer 4 illustrated herein can be of a number of convenient forms. For example, this layer may be comprised of one layer comprising one or more hole transport components, at least one of which is a silicon bridged indenofluorene compound. In an exemplary embodiment, layer 4 may be a laminate formed from a layer 4a in contact with the anode, and which layer contains a component which facilitates hole injection, and a layer 4b containing the a silicon bridged indenofluorene hole transport component.

Any suitable materials which can inject holes from the anode may be employed in layer 4a, with the preferred materials being the porphyrin derivatives as disclosed in U.S. Pat. No. 4,720,432, the disclosure of which is fully incorporated herein by reference. Representative examples of porphyrin derivatives are porphyrin; 1,10,15,20-tetraphenyl-21H,23H-porphyrin copper (II); copper phthalocyanine, copper tetramethyl phthalocyanine; zinc phthalocyanine; titanium oxide phthalocyanine; magnesium phthalocyanine; and the like.

Some exemplary silicon bridged indenofluorene compounds of Formula (I) that may be used as hole transporting compounds are:

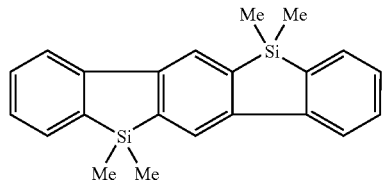

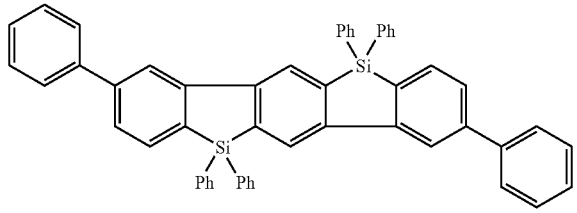

Similarly, the electron transporting layer 5 may be of a number of different convenient forms of, for example, a single layer, a dual layer, and the like. Any suitable electron transport compounds may be utilized in this zone. This layer may be comprised of one layer having one or more electron transport components, at least one of which is a boron bridged indenofluorene compound. In one exemplary embodiment, layer 5 may be a laminate formed from a layer 5a in contact with the cathode, and which layer contains a component which facilitates electron transport, and a layer 5b containing the boron bridged indenofluorene electron transporting component.

Examples of useful electron transport compounds include fused ring luminescent materials, such as anthracene, phenathrecene, pyrene, perylene, and the like as illustrated in U.S. Pat. No. 3,172,862; utadienes such as 1,4-diphenylbutadiene and tetraphenylbutadiene, and stilbenes, and the like as illustrated in U.S. Pat. Nos. 4,356,429 and 5,516,577; optical brightness such as those disclosed by U.S. Pat. No. 4,539,507. The disclosure of each of these patents is fully incorporated herein by reference.

Some exemplary boron bridged indenofluorene compounds of general Formula (II) that may be used as electron transporting compounds are:

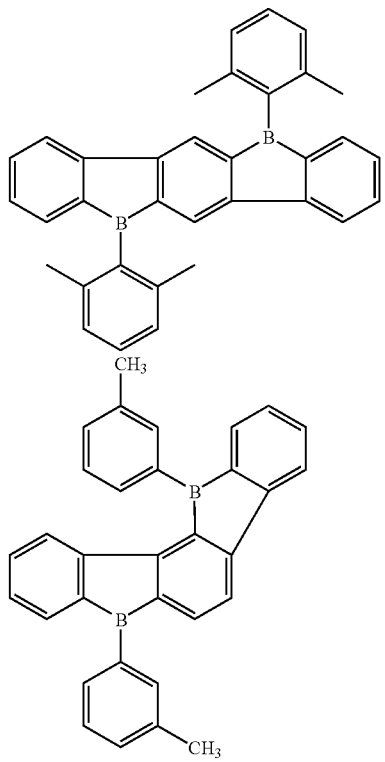

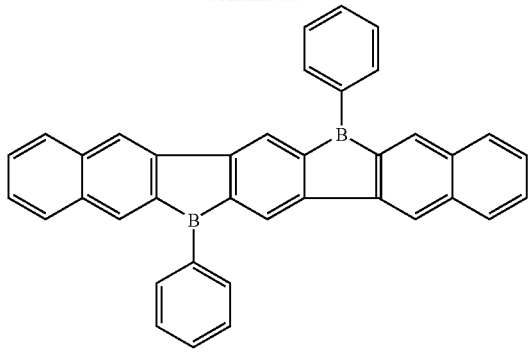

Additional electron transport materials are metal chelates of 8-hydroxyquinoline as disclosed in U.S. Pat. Nos. 4,539, 507; 5,151,629, and 5,150,006, the disclosures of which are fully incorporated herein by reference. Illustrative examples of the metal chelates include tris(8-hydroxyquinolinate)aluminum ($AlQ_3$), tris(8-hydroxyquinolinate)gallium, bis(8-hydroxyquinolinate)magnesium, bis(8-hydroxyquinolinate) zinc, tris(5-methyl-8-hydroxyquinolinate)aluminum, tris(7-propyl-8-quinolinolato) aluminum, bisubenzo {f}-8-quinolinate!zinc, bis(10-hydroxybenzo[h]quinolinate) berryllium, bis(2-methylquinolinolato) aluminum(III)-μ-oxo-bis(2-methyl-8-quinolinolato)aluminum(III), bis(2-methyl-8-quinolinolato) (phenolato)aluminum, bis(2-methyl-8-quinolinolato) (para-phenylphenolato) aluminum, bis(2-methyl-8-quinolinolato) (2-naphthalolato)aluminum, and the like.

Another class of electron transport materials is the metal chelates disclosed in U.S. Ser. No. 829,398, the disclosure of which is fully incorporated herein by reference, and represented by the following formula $$L_n-M^{+n} \quad (III)$$

wherein M represents a metal, n is a number of, for example, from 1 to 3, and L is a ligand as represented by Formula

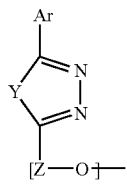

wherein Ar is an aryl group containing, for example, 6 to about 30 carbon atoms or an aromatic heterocyclic group, such as for example pyridyl, quinolyl, thienyl and the like; Y is selected from the group consisting of oxygen, sulfur, and selenium; N is nitrogen, O is oxygen, and Z is an aromatic component, such as for example 1,2-phenylene, 1,2-naphthylene, 2,3-naphthylene, 3,4-pyridinediyl, 3,4-quinolinediyl, the substituted analogs thereof with the substituents being preferably alkyl containing 1 to about 5 carbon atoms, phenyl or aryl with a substituent of halogen, alkyl or alkoxy groups containing 1 to 5 carbons, halogen, alkoxy groups containing 1 to 3 carbon atoms, a carboxy group, a cyano group, and the like.

The metal ion of Formulas (III) may be monovalent, divalent, or trivalent. Illustrative examples of metal ions include those which are capable of forming a stable chelate compound with the ligand, such as for example lithium, sodium, beryllium, magnesium, zinc, and the like, with the preferred metal ions being beryllium and zinc. Illustrative examples of metal chelate compounds (III) include bis[2-(2-hydroxyphenyl)-5-phenyl-1,3,4-oxadiazolato]zinc; bis[2-(2-hydroxyphenyl)-5-phenyl-1,3,4-oxadiazolato]berryllium; bis[2-(2-hydroxyphenyl)-5-(1-naphthyl)-1,3,4-oxadiazolato]zinc; bis>2-(2-hydroxyphenyl)-5-(1-naphthyl)-1,3,4-oxadiazolato!bberylium; bis[5-biphenyl-2-(2-hydroxyphenyl)-1,3,4-oxadiazolato]zinc; bis[5-biphenyl-2-(2-hydroxyphenyl)-1,3,4-oxadiazolato]beryllium; bis[(2-hydroxyphenyl)-5-phenyl-1,3,4-oxadiazolato]lithium; bis[2-(2-hydroxyphenyl)-5-p-tolyl-1,3,4-oxadiazolato]zinc; bis[2-(2-hydroxyphenyl)-5-p-tolyl-1,3,4-oxadiazolato]beryllium; bis[5-p-tert-butylphenyl)-2-(2-hydroxyphenyl)-1,3,4-oxadiazolato]zinc; bis[5-p-tert-butylphenyl)-2-(2-hydroxyphenyl)-1,3,4-oxadiazolato]beryllium; bis[2-(2-hydroxyphenyl)-5-(3-fluorophenyl)-1,3,4-oxadiazolato]zinc; bis[2-(2-hydroxyphenyl)-5-(4-fluorophenyl)-1,3,4-oxadiazolato]zinc; bis[2-(2-hydroxyphenyl)-5-(4-fluorophenyl)-1,3,4-oxadiazolato]beryllium; bis[5-(4-chlorophenyl)-2-(2-hydroxyphenyl)-1,3,4-oxadiazolato]zinc; bis[2-(2-hydroxyphenyl)-5-(4-methoxyphenyl)-1,3,4-oxadiazolato]zinc; bis[2-(2-hydroxy-4-methylphenyl)-5-phenyl-1,3,4-oxadiazolato]zinc; bis[2-α-(2-hydroxynaphthyl)-5-phenyl-1,3,4-oxadiazolato]zinc; bis[2-(2-hydroxyphenyl)-5-p-pyridyl-1,3,4-oxadiazolato]zinc; bis[2-(2-hydroxyphenyl)-5-p-pyridyl-1,3,4-oxadiazolato]beryllium; bis[2-(2-hydroxyphenyl)-5-(2-thiophenyl)-1,3,4-oxadiazolato]zinc; bis[2-(2-hydroxyphenyl)-5-phenyl-1,3,4-thiadiazolato]zinc; bis[2-(2-hydroxyphenyl)-5-phenyl-1,3,4-thiadiazolato]beryllium; bis[2-(2-hydroxyphenyl)-5-(1-naphthyl)-1,3,4-thiadiazolato]zinc; bis[2-(2-hydroxyphenyl)-5-(1-naphthyl)-1,3,4-thiadiazolato] beryllium; and the like.

These compounds offer a number of advantages as illustrated herein in that, for example, they possess a relatively high glass transition temperature, and are capable of forming thermally and morphologically stable thin films by vacuum evaporation techniques.

In yet another embodiment of the present invention, only one of the hole transporting layer 4 and the electron transporting layer 5 contains the respective indenofluorene compounds of the present invention. It is within the scope of the present invention that any combination of layers may be used.

As such, in some exemplary embodiments, only the hole transporting zone 4 contains a silicon bridged indenofluorene compound of the formulas illustrated herein. In some other exemplary embodiments, only the electron transporting zone 5 contains a boron bridged indenofluorene compound of the formulas illustrated herein. Additionally, in some exemplary embodiments both transporting layers contain the indenofluorene compound of the formulas illustrated herein, wherein the hole transporting layer would contain the silicon bridged compound and the electron transporting layer would contain the boron bridged compound. Furthermore, in some embodiments only one layer is used between the anode and cathode and such layer contains the indenofluorene compound of the formulas illustrated herein.

As used in this specification, the word "containing" means that the indenofluorene compound may either be present: 1) as a dopant in one or more layers, 2) as one or more layers, or 3) any combination thereof.

In embodiments of the present invention, the total thickness of the luminescent medium, which includes the hole transporting layer 4 and the electron transporting zone 5, is preferably less than about 1 micron to, for example, maintain a current density conducive to efficient light emission under a relatively low applied voltage across the electrodes. Suitable thickness of the hole transporting zone can range from about 50 to about 2,000 Angstroms, with the preferred thickness being from about 400 to about 1,000 Angstroms. Similarly, the thickness of the electron transporting zone can range from about 50 to about 2,000 Angstroms, with the preferred thickness being from about 400 to about 1,000 Angstroms. Each of the layers between the anode and cathode, such as the hole transport and electron transport layers, can be of various suitable thicknesses, such as from about 50 to about 125 nanometers.

The cathode 6 can be comprised of any suitable metal, including high, for example from about 4.0 eV to about 6.0 eV, or low work function metals, such as metals with, for example, an eV of from about 2.5 eV to about 4.0 eV (electron volts). The cathode can be derived from a combination of a low work function metal (less than about 4 eV) and at least one other metal. Effective proportions of the low work function metal to the second or other metal are from less than about 0.1 percent to about 99.9 percent by weight. Illustrative examples of low work function metals include alkaline metals such as lithium or sodium, Group 2A or alkaline earth metals such as beryllium, magnesium, calcium, or barium, and Group III metals including rare earth metals and the actinide group metals such as scandium, yettrium, lanthanum, cerium, europium, terbium, or actinium. Lithium, magnesium and calcium are the preferred low work function metals in embodiments of the present invention.

The thickness of cathode 6 ranges from, for example, about 10 to about 5,000 Angstroms. The Mg:Ag cathodes, reference U.S. Pat. No. 4,885,211, constitute one preferred cathode. Another preferred cathode construction is described in U.S. Pat. No. 5,429,884, wherein the cathodes are formed from lithium alloys with other high work function metals such as aluminum and indium. The disclosure of each of these patents is fully incorporated herein by reference.

Both anode 3 and cathode 6 of the EL devices of the present invention can be of any convenient forms. A thin conductive layer can be coated onto a light transmissive substrate, for example a transparent or substantially transparent glass plate or plastic film. The EL device can include a light transmissive anode 3 formed from tin oxide or indium tin oxide coated on a glass plate. Also, very thin, for example less than about, or equal to about 200 Angstroms, light-transparent metallic anodes can be used, such as gold, palladium, and the like. In addition, transparent or semitransparent thin layers, such as about 40 to about 100 nanometers, of conductive carbon or conjugated polymers, such as polyaniline, polypyrrole, and the like, can be selected as anodes. Any suitable light transmissive polymeric film can be employed as the substrate. Additional suitable forms of the anode 3 and cathode 6 are illustrated by U.S. Pat. No. 4,885,211.

The indenofluorene compound can be prepared by various suitable methods, for example it can be prepared by the preparation of the diazonium salt of 2-bromophenylamine and then a coupling reaction with phenylquinone to give the diarylquinone as described previously (Brassard and L'Ecuyer, Can. J Chem., 1958, Volume 36, pages 709-711). The quinone is then brominated with phosphorous pentabromide. This compound is then reacted with butyllithium and the appropriate silane or boron compound to give the desired product. Examples of appropriate silanes would include but is not limited to chlorodimethylsilane, chlorodiphenylsilane, dichloromethyloctylsilane, chloro(diisopropyl)silane, dichloromethylphenylsilane, dichloro-4-tolylsilane, diphenyldiacetatesilane or diphenyldimethoxysilane and examples of appropriate boron compounds would include, but is not limited to, phenylboron dichloride, 4-tolylboron dichloride, xylylboron dichloride or 2,5-dimethylphenylboron dichloride.

Exemplary polymerization processes are illustrated below:

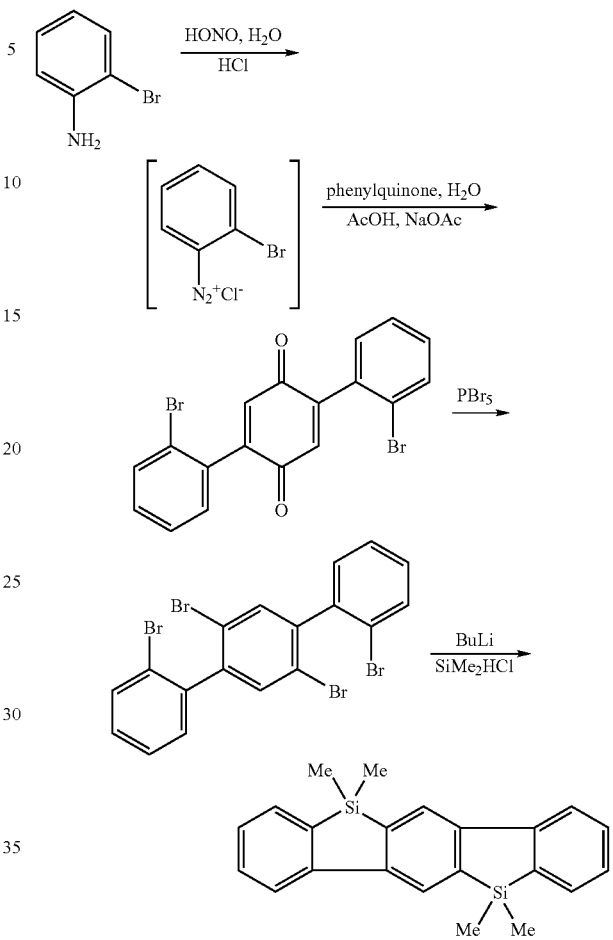

The substituents, such as for example $R^3$ and $R^4$, can be positioned at various different appropriate locations on the aromatic components, like the benzene ring.

It will be apparent to those skilled in the art that various modifications and variations can be made in the present invention without departing from the spirit or scope of the invention. Thus, it is intended that the present invention cover the modifications and variations of this invention provided they come within the scope of the appended claims and their equivalents.

The invention claimed is:

1. An organic electroluminescent device comprising:
an anode,
a cathode, and
a compound selected from one of Formula I and Formula II:

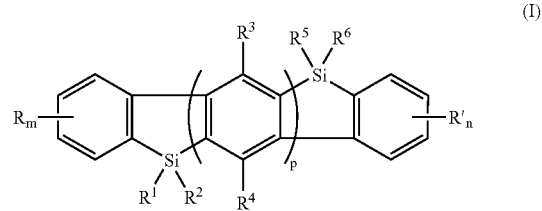

-continued

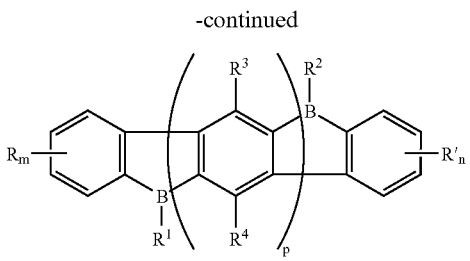

(II)

wherein R and R' are independently selected from the group consisting of a hydrogen atom, halogen atom, cyano, alkyl, alkoxyl, alicyclic alkyl, unsubstituted aryl or heteroaryl, and dialkylamino; m and n are numbers of 0 to 4; $R^1$, $R^2$, $R^5$, and $R^6$ are independently selected from the group consisting of hydrogen, an alkyl, a substituted or unsubstituted aryl, or an heteroaryl, an alkoxy, and vinyl; $R^3$ and $R^4$ are independently selected from the group consisting of a hydrogen atom, halogen atom, alkyl, alkoxy, and substituted or unsubstituted aryl or heteroaryl; and p is 1 or greater.

2. The electroluminescent device of claim 1, wherein the aryl in the compound of Formula I or Formula II is a fused aromatic ring.

3. The electroluminescent device of claim 2, wherein said fused ring is benzo.

4. The electroluminescent device of claim 1, wherein the alkyl in the compound of Formula I or Formula II contains from 1 to about 25 carbon atoms, alkoxy contains from 1 to about 25 carbon atoms, and aryl contains from 6 to about 30 carbon atoms.

5. The electroluminescent device of claim 1, wherein the alkyl in the compound of Formula I or Formula II contains from 1 to about 10 carbon atoms, alkoxy contains from 2 to about 12 carbon atoms, and aryl contains from 6 to about 18 carbon atoms.

6. The electroluminescent device of claim 1, wherein the alkyl in the compound of Formula I or Formula II contains from 1 to about 6 carbon atoms, and wherein alkoxy contains from 1 to about 6 carbon atoms.

7. The electroluminescent device of claim 1, wherein the alkyl in the compound of Formula I or Formula II is methyl, ethyl, propyl, butyl, pentyl, heptyl, or hexyl, and wherein alkoxy is methoxy, ethoxy, propoxy, butoxy, pentoxy, or heptoxy.

8. The electroluminescent device of claim 1, wherein the said halogen atom in the compound of Formula I or Formula II is an atom of chlorine, bromine, fluorine, or iodine.

9. The electroluminescent device of claim 1, wherein the aryl in the compound of Formula I or Formula II is phenyl.

10. The electroluminescent device of claim 1, wherein the compound is of Formula I, R and R' are hydrogen, or alkyl, and $R^1$, $R^2$, $R^5$, and $R^6$ are aryl.

11. The electroluminescent device of claim 10, wherein R and R' are hydrogen, or alkyl, and $R^3$ and $R^4$ are hydrogen atoms.

12. The electroluminescent device of claim 1, wherein the compound is of Formula II, R and R' are hydrogen, or alkyl, and $R^1$ and $R^2$ are aryl.

13. The electroluminescent device of claim 12, wherein R and R' are hydrogen, or alkyl, and $R^3$ and $R^4$ are hydrogen atoms.

14. The electroluminescent device of claim 1, wherein $R^1$, $R^2$, $R^5$, and $R^6$ are independently selected from the group consisting of phenyl, naphthyl, thienyl and biphenyl.

15. The electroluminescent device of claim 1, wherein the compound is of Formula I,
the aryl in the compound of Formula I contains from 6 to about 30 carbons;
$R^1$, $R^2$, $R^5$, and $R^6$ are aryl groups;
R and R' are hydrogen atoms or methyl groups; and
$R^3$ and $R^4$ are hydrogen atoms.

16. The electroluminescent device of claim 1, wherein the compound is Formula II,
the aryl in the compound of Formula II contains from 6 to about 30 carbons;
$R^1$ and $R^2$ are aryl groups;
R and R' are hydrogen atoms or methyl groups; and
$R^3$ and $R^4$ are hydrogen atoms.

17. The electroluminescent device of claim 1, further comprising:
a supporting substrate;
a hole transporting layer with a thickness ranging from about 10 nanometers to about 100 nanometers;
an electron transporting layer with a thickness ranging from about 10 nanometers to about 100 nanometers; and
wherein said anode is comprised of a layer of indium tin oxide with a thickness ranging from about 30 nanometers to about 100 nanometers, said cathode is a magnesium/silver alloy or a lithium/aluminum alloy, with a thickness ranging from about 10 nanometers to about 200 nanometers, and wherein at least one of the hole transporting layer and electron transporting layer contains indenofluorene compound, wherein the compound is of Formula I when it is used as a hole injecting layer, and wherein the compound is of Formula II when it is used as an electron transporting layer with a thickness ranging from about 10 nanometers to about 100 nanometers.

18. An organic electroluminescent compound comprising Formula I:

Formula I

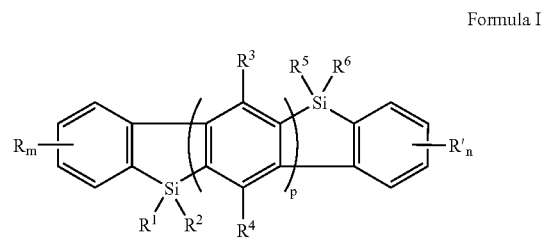

wherein R and R' are independently selected from the group consisting of a hydrogen atom, halogen atom, cyano, alkyl, alkoxyl, alicyclic alkyl, unsubstituted aryl or heteroaryl, and dialkylamino; m and n are numbers of 0 to 4; $R^1$, $R^2$, $R^5$, and $R^6$ are independently selected from the group consisting of hydrogen, an alkyl, a substituted or unsubstituted aryl, or an heteroaryl, an alkoxy, and vinyl; $R^3$ and $R^4$ are independently selected from the group consisting of a hydrogen atom, halogen atom, alkyl, alkoxy, and substituted or unsubstituted aryl or heteroaryl; and p is 1 or greater.

19. The compound of claim 18, wherein the aryl is a fused aromatic ring.

20. The compound of claim 19, wherein said fused ring is benzo.

21. The compound of claim 18, wherein the alkyl contains from 1 to about 25 carbon atoms, alkoxy contains from 1 to about 25 carbon atoms, and aryl contains from 6 to about 30 carbon atoms.

22. The compound of claim 18, wherein the alkyl contains from 1 to about 10 carbon atoms, alkoxy contains from 2 to about 12 carbon atoms, and aryl contains from 6 to about 18 carbon atoms.

23. The compound of claim 18, wherein the alkyl contains from 1 to about 6 carbon atoms, and wherein alkoxy contains from 1 to about 6 carbon atoms.

24. The compound of claim 18, wherein the alkyl is methyl, ethyl, propyl, butyl, pentyl, heptyl, or hexyl, and wherein alkoxy is methoxy, ethoxy, propoxy, butoxy, pentoxy, or heptoxy.

25. The compound of claim 18, wherein the said halogen atom is an atom of chlorine, bromine, fluorine, or iodine.

26. The compound of claim 18, wherein the aryl is phenyl.

27. The compound of claim 18, wherein R and R' are hydrogen, or alkyl, and $R^1$, $R^2$, $R^5$, and $R^6$ are aryl.

28. The compound of claim 18, wherein R and R' are hydrogen, or alkyl, and $R^3$ and $R^4$ are hydrogen atoms.

29. The compound of claim 18, wherein $R^1$, $R^2$, $R^5$, and $R^6$ are independently selected from the group consisting of phenyl, naphthyl, thienyl and biphenyl.

30. The compound of claim 18, wherein the
aryl in the compound of formula I contains from 6 to about 30 carbons;
$R^1$, $R^2$, $R^5$, and $R^6$ are aryl groups;
R and R' are hydrogen atoms or methyl groups; and
$R^3$ and $R^4$ are hydrogen atoms.

31. An organic electroluminescent compound comprising Formula II:

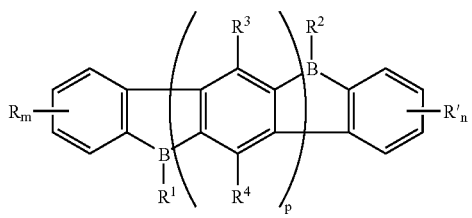

Formula II wherein R and R' are independently selected from the group consisting of a hydrogen atom, halogen atom, cyano, alkyl, alkoxyl, alicyclic alkyl, unsubstituted aryl or heteroaryl, and dialkylamino; m and n are numbers of 0 to 4; $R^1$ and $R^2$ are independently selected from the group consisting of hydrogen, an alkyl, a substituted or unsubstituted aryl, or an heteroaryl, an alkoxy, and vinyl; $R^3$ and $R^4$ are independently selected from the group consisting of a hydrogen atom, halogen atom, alkyl, alkoxy, and substituted or unsubstituted aryl or heteroaryl; and
p is 1 or greater.

32. The compound of claim 31, wherein the aryl is a fused aromatic ring.

33. The compound of claim 32, wherein said fused ring is benzo.

34. The compound of claim 31, wherein the alkyl contains from 1 to about 25 carbon atoms, alkoxy contains from 1 to about 25 carbon atoms, and aryl contains from 6 to about 30 carbon atoms.

35. The compound of claim 31, wherein the alkyl contains from 1 to about 10 carbon atoms, alkoxy contains from 2 to about 12 carbon atoms, and aryl contains from 6 to about 18 carbon atoms.

36. The compound of claim 31, wherein the alkyl contains from 1 to about 6 carbon atoms, and wherein alkoxy contains from 1 to about 6 carbon atoms.

37. The compound of claim 31, wherein the alkyl is methyl, ethyl, propyl, butyl, pentyl, heptyl, or hexyl, and wherein alkoxy is methoxy, ethoxy, propoxy, butoxy, pentoxy, or heptoxy.

38. The compound of claim 31, wherein the said halogen atom is an atom of chlorine, bromine, fluorine, or iodine.

39. The compound of claim 31, wherein the aryl is phenyl.

40. The compound of claim 31, wherein R and R' are hydrogen, or alkyl, and $R^1$ and $R^2$ are aryl.

41. The compound of claim 31, wherein R and R' are hydrogen, or alkyl, and $R^3$ and $R^4$ are hydrogen atoms.

42. The compound of claim 31, wherein $R^1$ and $R^2$ are independently selected from the group consisting of phenyl, naphthyl, thienyl and biphenyl.

43. The compound of claim 31, wherein the
aryl in the compound of formula II contains from 6 to about 30 carbons;
$R^1$ and $R^2$ are aryl groups;
R and R' are hydrogen atoms or methyl groups; and
$R^3$ and $R^4$ are hydrogen atoms.

\* \* \* \* \*